United States Patent [19]

Healy et al.

[11] 4,090,849

[45] May 23, 1978

[54] DIAGNOSTIC DEVICE AND MANUFACTURE THEREOF

[75] Inventors: William A. Healy, Ballston Lake; William J. Ward, III; David A. Vermilyea, both of Schenectady, all of N.Y.

[73] Assignee: General Electric Company, Schenectady, N.Y.

[21] Appl. No.: 752,186

[22] Filed: Dec. 20, 1976

[51] Int. Cl.² ............................................. G01N 33/16
[52] U.S. Cl. .............................. 23/253 TP; 23/230 B; 23/259; 156/664; 424/12
[58] Field of Search .............. 23/230 B, 253 TP, 259; 424/12; 428/434

[56] References Cited

U.S. PATENT DOCUMENTS

| | | | |
|---|---|---|---|
| 3,853,467 | 12/1974 | Giaever | 23/230 B |
| 3,926,564 | 12/1975 | Giaever | 428/434 X |
| 3,979,184 | 9/1976 | Giaever | 23/253 TP |
| 3,979,509 | 9/1976 | Giaever | 23/230 B X |
| 4,041,146 | 8/1977 | Giaever | 23/230 B X |
| 4,054,646 | 10/1977 | Giaever | 23/230 B X |

*Primary Examiner*—Sidney Marantz
*Attorney, Agent, or Firm*—L. I. MaLossi; J. T. Cohen; M. Snyder

[57] ABSTRACT

Clinically useful diagnostic devices are prepared from commercially available metal sheet stock by a sequence of steps. The metal is one of a type on the surface of which a tenacious oxide layer can be produced. Steps in the preparation include roughening surface area of the bulk metal with pits on a fine scale to render that surface area of the metal non-specularly reflecting, chemically etching the surface area to produce some first preselected measure of reflectivity, anodizing the surface area to produce a dull, non-specularly reflecting oxide surface having a second preselected degree of reflectivity and applying a layer of protein over this dull surface area. The preferred metal is titanium and the reflectivity of the modified surface area is selected dependent on the immunological reaction being detected.

11 Claims, 4 Drawing Figures

DIAGNOSTIC DEVICE AND MANUFACTURE THEREOF

BACKGROUND OF THE INVENTION

This invention relates to devices for the clinical detection of biological particles by the utilization of the phenomenon by which such biological particles interact specifically either immunologically or non-immunologically.

Constructions of diagnostic devices for use in the immunological detection of proteins are disclosed in U.S. patent application Ser. No. 384,113 — Giaever, filed July 30, 1973 (now abandoned) and U.S. Pat. No. 3,926,564 — Giaever. In both of these constructions the outer surface consists of a layer of preselected proteins specifically interactive with the protein of interest. In Ser. No. 384,113, the substrate surface to which the preselected protein layer is applied is preferably a metallic coating on a glass substrate. In U.S. Pat. No. 3,926,564, the surface to which the preselected protein layer is applied is made up predominately of metallic oxide, which metallic oxide may contain minute metallic particles. The aforementioned application was assigned to the assignee of this invention. Both the aforementioned Giaever patent and Giaever application are incorporated herein by reference.

In still another diagnostic device described and claimed in U.S. Pat. No. 3,979,184 — Giaever, a non-transparent surface of metal (solid metal or non-transparent coating of metal on a different substrate), which is a comparatively poor reflector of light, is covered with a thin transparent first layer of dielectric material. This first layer, in turn, has a transparent second layer of metal adhered over the outer surface thereof. U.S. Pat. No. 3,979,184 is also incorporated by reference.

Most antigens are proteins or contain proteins as an essential part, whereas all antibodies are proteins. Proteins are large molecules of high molecular weight, i.e., are polymers consisting of chains of variable numbers of amino acids. A given proteinaceous material will comprise entities (e.g., protein molecules, cells, etc.), which do not adhere to each other. Therefore, when a proteinaceous material is brought into contact with a substrate, it deposits as a single layer. If the entities are molecular in size, the resulting single layer is monomolecular. No other arbitrary protein will adhere to an already deposited protein layer. On the other hand, a protein that is specifically reactive relative to a protein that has been adsorbed onto the substrate will immunologically bond thereto. In accordance with the teachings of the above-cited applications, this discovery is exploited to provide medical diagnostic apparatus in which a slide having a first layer of one protein adsorbed thereon is used to test suspected solutions for the presence of the protein specifically reactive thereto. If the specifically reactive protein is present in the solution, the slide (after exposure to the solution) will have a double protein layer thereon. If the specifically reactive protein be absent from the solution, the slide (after exposure to the solution) will have only the original layer thereon.

The term "biological particle" is intended to encompass smaller proteins (e.g., plasma proteins, antigens, antibodies, lactins) and bodies of proteinaceous material (e.g., viruses, bacteria, cells) capable of stimulating antibody production, when injected into an animal, and/or having the property of interacting specifically either immunologically or non-immunologically.

The term "antigenic material" and the term "antigenically active material" describe material containing antigenic sites such as may be derived from viruses, bacteria, etc.

Reference herein to "visual readout" means readout that can be accomplished by a person with normal vision (or vision correctible to 20/40) who is not color blind and is unaided by instrumentation.

DESCRIPTION OF THE INVENTION

Clinically useful diagnostic devices are prepared from commercially available metal sheet stock by a sequence of steps. The metal is one on the surface of which a tenacious oxide layer can be produced. Steps in the preparation include roughening surface area of the bulk metal to render that surface area of the metal non-specularly reflecting, chemically etching the surface area to produce some first preselected measure of reflectivity, treating the surface area to produce a dull, non-specularly reflecting oxide surface having a second preselected degree of reflectivity and applying a layer of protein over this dull surface area. The preferred metal is titanium and the reflectivity of the modified surface area is selected dependent on the immunological reaction being detected. The matted, non-specularly reflecting finish provided for the modified surface area has the distinct advantage that bilayer spots developed thereon (e.g., from an antibody-antigen reaction) can be easily seen with the unaided eye from any viewing angle without special lighting.

BRIEF DESCRIPTION OF THE DRAWINGS

The subject matter of the instant invention for which protection is sought is presented as claims at the conclusion of the written description of the invention set forth herein. The description sets forth the manner and process of making and using the invention and the accompanying drawing forms part of the description.

MANNER AND PROCESS OF MAKING AND USING THE INVENTION

Figure 1:
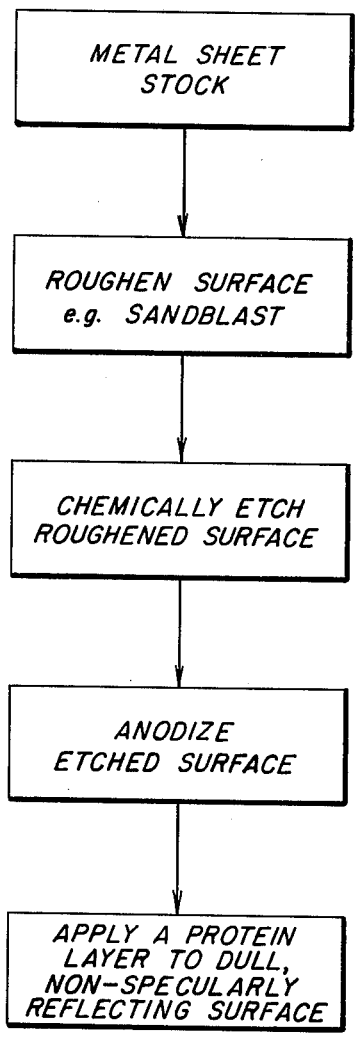
FIG. 1 sets forth a flow sheet describing the manufacturing process of this invention.
Figure 2:
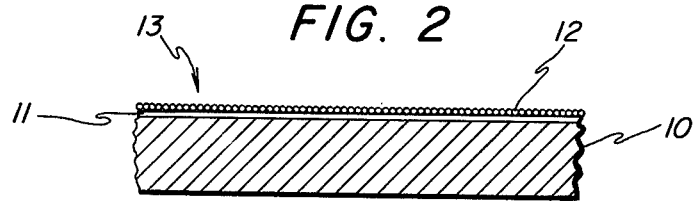
FIG. 2 schematically displays a cross-section taken through the diagnostic device of this invention.
Figure 3:
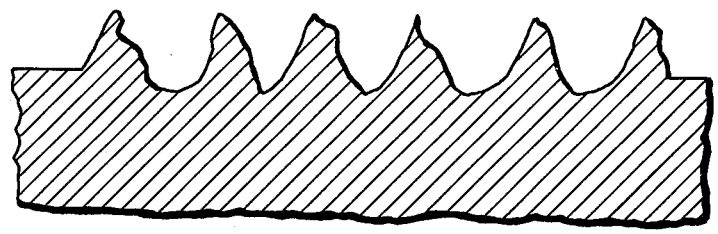
FIG. 3 is a view in cross-section schematically representing the upset, or roughened, surface of the bulk metal produced.
Figure 4:
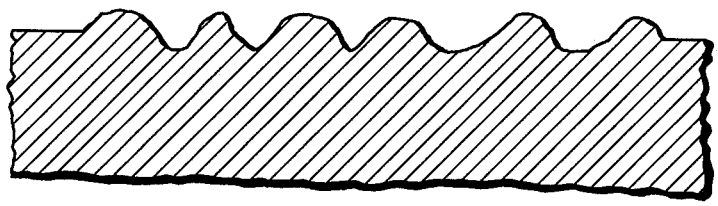
FIG. 4 is a view similar to FIG. 3 to show the change effectuated by the etching step.

Referring to FIGS. 1 and 2 of the drawings, thin (e.g., about 10 mils thick) commercially available solid metal sheet stock 10 is selected primarily on the basis of the capability for forming a tenacious oxide layer on the surface thereof. Examples of suitable single metals are titanium, tantalum, niobium, tungsten, zirconium, and bismuth. It is expected that various alloys may also be suitable. The tenacity (or adherence) of the oxide layer (and the inertness thereof) is evaluated on the basis of whether it will survive manufacture and use of the clinical device being produced. Having selected an appropriate substrate metal, the first step is to surface blast area thereof with fine (e.g., in the range of 320 alumina to 600 carborundum) grit to render the selected area non-specularly reflective. As shown in FIG. 3 the surface blasted metal will have a relatively uniform distribution of pits. The spans and depths of these pits appears to be about 70,000 Angstroms or less (most are in the 5,000 – 70,000 A range) in dimension. This surface is next etched chemically with acid to reduce the extent of surface roughening (i.e., the degree to which metal is raised from the original surface by particle impingement thereon) as shown in FIG. 4 so as to produce some first preselected value of reflectivity.

In order to provide some objective standard for reproducing the degree of roughness and lightness of coloration desired for producing an acceptable diagnostic device, a properly calibrated Macbeth RD-100 Densitometer (Macbeth Instrument Corporation, Newburgh, New York) has been employed to measure the reflectance of the treated metal surface. Reflectance is measured in American Standards Association (ASA) Diffuse Reflection Density. The meter scale on this particular instrument provides a linear measure of optical diffuse reflection density and the density graduations are equally spaced. A selection of filters is provided for the particular light source utilized. The values for density units given herein were for a General Electric tungsten anti-fatigue lamp No. 40 (6.3 volts, 0.15 amps) coupled with the "visual" (Wratten No. 106W, Eastman Kodak) filter. The conditions of measurement employed were in accordance with ASA specification PH.2.17.-1958. Values comparable to the values provided herein can, of course, be readily determined for other densitometers.

Using the Macbeth unit, slides chemically etched to a reflectivity in the range of from about 0.3 to 0.5 Density Units (D.U.) have proven satisfactory for the first preselected value of reflectivity. The lower the value of the D.U., the lighter the appearance of the surface.

Chemical etching is accomplished in an acidic bath, preferably a heated bath employing two or more acids from the group consisting of $H_2SO_4$, $HNO_3$ and HF. The acids selected, the proportions employed and the temperature of the bath will vary with the particular metal selected for the substrate and the period of time considered optimum for the manufacturing process. Useful etching baths are determinable by routine experimentation from guidelines provided herein. It has been found that by using ultrasound during the etching step a cleaner product results. One acid bath found useful for titanium, tantalum and niobium substrates is a 3% (by volume) solution of equal volumes of HF and $HNO_3$ heated to 35° C.

Thereafter the chemically-etched sheet is anodized to produce an oxide layer 11 (FIG. 2) having a thickness in the range of from about 100 Angstroms to about 500 Angstroms whereby the previously treated surface acquires a matte finish and is non-specularly reflecting. The preferred thickness of the oxide layer is in the range of from about 250 A to about 300 A.

The thickness of the oxide layer to be used is such as to produce a second preselected value of reflectivity, which value in turn is selected knowing what given layer of protein material is to be deposited thereon and the color change that can be expected from the reaction to be detected. It has been found that in general for larger protein molecules the useful post-anodizing reflectivity may range down to 0.50 D.U. or less while for smaller protein molecules the useful post-anodizing reflectivity may be as much as about 0.85 D.U. In preparing a diagnostic device for the detection of a specific reaction, the second preselected value of reflectivity will be numerically greater than the first preselected value.

Although production of the oxide layer is most conveniently accomplished by anodizing, it is feasible to carry on the oxidation step by heating in an oxidizing environment. Useful reference texts for anodizing are "Anodic Oxide Films" — L. Young (Academic Press 1961) and "Introduction to Organic Electrochemistry" — M. R. Rife and F. Kovitz (Marcel Dekker Inc. 1974).

In order to produce various desired values of reflectivity utilizing a given anodizing bath, all that is necessary is to change the voltage, i.e., a lower voltage produces a lighter colored slide. Thus, for tantalum substrates a 0.2 V change in voltage produced a 3–4 A change in oxide layer thickness. Because, of this sensitivity to voltage fluctuations, these fluctuations should be minimized by using appropriate circuitry. Once a given value has been set for the second preselected value of reflectivity, subsequent anodizing is carried to this value.

The resulting oxide-covered metal surface next receives a layer 12 of protein (e.g., a layer of antigenically active material) as is shown in FIG. 2 over at least a portion of the treated area of metal, which protein will interact specifically with select biological particles upon exposure thereto. After rinsing, the diagnostic device 13 is ready for use and may be packaged for sale.

In use, sample liquid to be tested for the presence of select biological particles is deposited (e.g., as discrete drops) on a portion of the initial (specific) protein layer. If select biological particles are present, they interact with the specific protein and, where this contact occurs, a bilayer of protein develops. This bilayer area(s) should be readily visible by color contrast to the unaided eye against the monolayer of protein on the dull, light-colored non-specularly reflecting surface, if the proper value has been selected for the second preselected value of reflectivity. In the absence of select biological particles no second layer develops, of course.

This procedure is equally applicable either to discrete pieces of metal (e.g., 1 inch × 2 inch × 10 mil thick) or to continuous metal ribbon (e.g., 1 inch wide × 10 mil thick).

The prepared substrate (i.e., prior to applying the layer of protein to generate the diagnostic device of this invention) is broadly applicable in the detection of the phenomenon by which biological particles interact specifically. The preferred construction of the diagnostic device of this invention is that in which layer 12 is a layer of antigenic material.

It is but a simple matter to select the level of the second value of preselected reflectivity to be used for the anodized surface for a given specific reaction. Thus, having selected the specific reaction and starting with a metal substrate prepared as described herein so as to present an anodized surface having a reflectivity of 0.80 D.U., the proper initial layer and second layer of biological particles are applied and examined. If insufficient contrast results, a deduction can readily be made as to whether the reflectivity should be reduced (i.e., for lighter colored surface) or increased (i.e., for darker colored surface). Verification of the optimum reflectivity for maximum contrast will follow from routinely varying the substrates subsequently prepared.

When metal slides have been prepared by only surface roughening (as described) and anodizing (as described), the results were dark slides providing poor spot contrast. This same result occurred, when metal slides were prepared by chemically etching (as described) and anodizing (as described). Good slides were prepared from titanium solely by anodizing the substrate, when the substrate had a very smooth surface, but visual readout was complicated by the need to tilt the slide to reflect light in just the right manner to be able to observe the bilayer spots created thereon.

With the method described herein, bilayer spots are readily visible from any angle on the non-specularly reflecting surface. The characteristic of being a non-specularly reflecting surface is due to the roughening-/etching sequence, of couse, while the lightness of coloration is dependent on the anodizing voltage applied.

BEST MODE CONTEMPLATED

Solid titanium sheet 10 mils in thickness is subjected to a vapor blast using 320 alumina, i.e., the fine alumina powder is entrained in water and ejected under pressure. The resulting surface is dark and non-specularly reflecting. Typical reflectivity of such a very uniformly roughened surface is about 0.70 D.U. and under magnification the outline of the resulting surface appears as shown in FIG. 3. The roughened titanium is chemically etched using a 3 percent (by volume) solution of approximately equal parts (by volume) of hydrofluoric and nitric acids heated to about 35° C. Depending upon the particular concentration of the etching solution, the etching (accompanied by the application of ultrasonic vibration) carried on for 30 to 90 seconds (preferably ~ 50 seconds) yields a non-specularly reflecting surface that is light silver in color. The modified surface profile is shown in FIG. 4 providing a reflectivity of 0.40 ± 0.02 D.U. Next, the titanium sheet is anodized at about 11.5 volts for about 15 seconds in a 0.29 molar ammonium pentaborate solution. Substrates anodized in this way develop an oxide layer about 300 A thick and have a reflectivity of 0.80 ± 0.02 D.U. and a bronze, or yellow/orange, hue.

In specific construction, titanium substrates so prepared have been provided with a first layer of bovine serum albumen (BSA), washed and then dried. The area covered by the BSA is barely detectable on the anodized surface. Next, the BSA layer was contacted with one or more drops of rabbit antiserum BSA (Miles Laboratory) and incubated for about 4 hours. The bi-layer spots clearly stand out, because they are of a reddish color contrasting markedly with the bronze colored BSA-covered layer.

What we claim as new and desire to secure by Letters Patent of the United States is:

1. A process for the production of a diagnostic device useful for detecting the presence or absence of select biological particles in a liquid sample comprising the steps of:
   roughening surface area on a bulk metal substrate to render said surface area non-specularly reflecting, the metal having the property of enabling the formation of a tenacious oxide layer on the surface thereof;
   chemically etching said surface area to yield therefor a first preselected value of reflectivity;
   oxidizing said surface area to produce thereon an oxide layer having a thickness in the range of from about 100 Angstroms to about 500 Angstroms and to change said first preselected value of reflectivity to a second and larger preselected value of reflectivity, said oxide layer being non-specularly reflecting; and
   applying a layer of protein over at least part of said oxide layer.

2. The process recited in claim 1 wherein the first preselected value of reflectivity is comparable to a value in the range of from about 0.30 to about 0.50 density units as measured on a Macbeth RD-100 densitometer using a visual filter.

3. The process recited in claim 3 wherein the roughening is in the form of pits, the span and depth of which are about 70,000 Angstroms or less in dimension.

4. The process recited in claim 1 wherein the metal is selected from the group consisting of titanium, tantalum, niobium, zirconium, and bismuth.

5. The process recited in claim 1 wherein the oxide layer is produced by anodizing.

6. The process recited in claim 5 wherein the anodizing step is conducted in an ammonium pentaborate solution.

7. The process recited in claim 1 wherein the second preselected value of reflectivity is comparable to a value in the range of from about 0.50 to about 0.85 density units as measured on a Macbeth RD-100 densitometer using a visual filter.

8. The process recited in claim 1 wherein the chemical etching is conducted in an acid bath, the content of which includes at least two acids selected from the group consisting of hydrofluoric, nitric and sulfuric.

9. The process recited in claim 1 wherein the thickness of the oxide layer is in the range of from about 250 Angstroms to about 300 Angstroms.

10. The process recited in claim 1 wherein the protein is an antigenically active material.

11. A diagnostic device prepared by the process of claim 1.

* * * * *